United States Patent [19]

Schroeder

[11] Patent Number: 5,671,695

[45] Date of Patent: Sep. 30, 1997

[54] REPLACEMENT LIGAMENT GRAFT PASSER AND METHOD

[75] Inventor: Frederick J. Schroeder, Winter Park, Fla.

[73] Assignee: DePuy Inc., Warsaw, Ind.

[21] Appl. No.: 281,742

[22] Filed: Jul. 28, 1994

[51] Int. Cl.$^6$ .................................................. A61B 19/00
[52] U.S. Cl. .............................. 128/897; 623/13; 623/20
[58] Field of Search ......................... 128/597–99; 623/11, 623/13, 16, 18–20, 39

[56] References Cited

U.S. PATENT DOCUMENTS

| D. 309,499 | 7/1990 | Bowman et al. | |
|---|---|---|---|
| 5,139,520 | 8/1992 | Rosenberg | 623/13 |
| 5,171,274 | 12/1992 | Fluckiger et al. | 623/11 |
| 5,320,115 | 6/1994 | Kenna | 623/20 |

OTHER PUBLICATIONS

"ACL Accessories", DePuy Brochure No. 20M0185 0606–29–000 (1995).
DePuy Inc. Brochure, "Steadman Ligament Graft Passer and Protector", 1990.

*Primary Examiner*—John P. Lacyk
*Attorney, Agent, or Firm*—Barnes & Thornburg

[57] ABSTRACT

An apparatus is provided for use in installing a replacement ligament in substantially coaxial tibial and femoral tunnels formed in a knee joint by drilling upwardly from the anterior surface of the tibia below its plateau, through the plateau, and into the distal end of the femur. The replacement ligament has a leading end portion receivable in the femoral tunnel and a trailing end portion receivable in the tibial tunnel. The apparatus includes a sheath having a leading open end and an opposite end. The sheath has a calibrated scale printed thereon starting at the leading open end. The calibrated scale provides a visual indication of a distance from the leading open end of the sheath. The sheath is configured to receive the replacement ligament therein while the sheath is outside a patient's body with the leading end portion of the replacement ligament adjacent said open end and with the trailing end portion of the replacement ligament disposed toward said opposite end of the sheath. The sheath is sized for insertion into the tibial tunnel to position the replacement ligament within the knee joint.

23 Claims, 5 Drawing Sheets

REPLACEMENT LIGAMENT GRAFT PASSER AND METHOD

BACKGROUND AND SUMMARY OF THE INVENTION

The present invention relates to a replacement ligament graft passer and method. More particularly, the present invention relates to a graft passer and surgical method which protects the replacement ligament during fixation of the ligament inside the femur and tibia bones of the knee joint with interference screws and which reduces the likelihood of divergence of the femoral interference screw used to secure a femoral portion of the replacement ligament graft in a drilled femoral tunnel.

When a ligament such as a anterior cruciate ligament (ACL) of a knee is damaged or torn, a replacement ligament is often installed in the knee to reconstruct the natural ACL. During such reconstruction, a tunnel is typically drilled through the anterior portion of the tibia upwardly through the tibial plateau and into the distal end of the femur to approximate the natural position of the ACL. A bone-ligament-bone graft is then harvested, often from the patellar tendon, following standard grafting procedures. Typically, a wedge-shaped graft is cut from the patella and from a top portion of the tibia to provide wedge-shaped bone plug segments on opposite ends of a ligament. The wedge-shaped graft is then sized using a standard graft sizer such as a DePuy Graft Sizer available from DePuy, Inc. in Warsaw, Ind. Sutural holes are then formed in each of the bone graft portions of the replacement ligament. Sutures are then often attached to each of the bone plug segments.

Various methods are known for securing the bone graft sections of the replacement ligament within the tibia and femur until the graft can heal. One such method is the use of Kurosaka™ fixation screw. The Kurosaka™ screw provides an interference fit inside a drilled femoral or tibial tunnel with a bone graft located therein so that the graft is wedged against the wall of the tunnel. See, for example, U.S. Pat. No. 4,950,270. In the '270 patent, Kurosaka™ screws are installed into a femoral bone bore hole and a tibial bone bore hole. In this instance, separate tibial and femoral tunnels are drilled.

The graft passer of the present invention is designed to improve installation of Kurosaka™ interference screws into tibial and femoral tunnels in which the femoral tunnel is not drilled entirely through the femur bone. Instead, standard drilling techniques are used to form a tibial tunnel which extends upwardly from an anterior portion of the tibia and through the tibial plateau using a drill guide. For an example of a variable angle selective length tibial drill guide, see U.S. Pat. No. 5,112,337. A femoral tunnel is drilled upwardly into the distal end of the femur through the intercondylar notch with the drill extending through the tibial tunnel. Typically, the femoral tunnel is reamed to a depth of about 5 mm longer than the length of the femoral bone graft. Using the surgical method of the present invention, the femoral tunnel does not extend through the anterolateral cortex of the femur. Therefore, the only access to the femoral tunnel for inserting a Kurosaka™ screw is adjacent the distal end of the femur. In conventional surgical methods, anchoring of the femoral bone graft within the femoral tunnel is done by fully flexing the knee and then inserting the Kurosaka™ screw through a separate incision located on the medial side of the knee. Such insertion through a separate incision makes it difficult or impossible to align a longitudinal axis of the interference fixation screw with a longitudinal axis of the femoral tunnel and bone graft thereon. Therefore, the axis of the interference screw tends to diverge away from the axis of the femoral tunnel and bone graft therein. This divergence reduces the fixation strength of the interference screw.

Advantageously, the graft passer of the present invention provides a protective tube or sheath for surrounding the replacement ligament. Therefore, a femoral interference screw can be inserted through the tibial tunnel with the graft passer and replacement ligament in place in the tunnel. The graft passer of the present invention provides protection for the replacement ligament from damage due to femoral interference screw insertion. By inserting the femoral interference screw through the tibial tunnel, the present invention advantageously aligns a longitudinal axis of the femoral interference screw with a longitudinal axis of the femoral tunnel and bone graft located therein. In other words, the longitudinal axis of the interference screw is parallel to and spaced apart from the longitudinal axis of the tunnel. By aligning the longitudinal axis of the interference screw parallel to a longitudinal axis of the femoral tunnel and femoral bone graft, the present invention advantageously provides the best angle of approach for inserting the femoral interference screw to secure the femoral bone plug along its entire length uniformly within the femoral tunnel. This reduces the likelihood of divergence of the interference screw in the femoral tunnel and improves fixation of the femoral bone plug inside the femoral tunnel.

Advantageously, the protective sheath of the graft passer of the present invention is transparent to permit viewing of the replacement ligament loaded inside the sheath. Also, advantageously, measurement calibrations are printed on the exterior surface of the protective sheath to provide a visual indication of the distance from a leading open end of the sheath down the length of the sheath. Advantageously, these calibrations on the sheath provide an easy method of tunnel length determination and for determining the length of the ligament replacement.

One type of ligament graft passer is known for use in the replacement ligament procedure which includes separately drilled tibial and femoral tunnels. In this instance, the tunnels are first drilled separately through the tibia and femur. A graft passer is then inserted through the drilled tunnels. A leader portion of the graft passer is then cut and a graft is passed through an open end of the graft passer through the anterolateral cortex of the femur through an incision in the thigh. After the replacement ligament is installed into the tunnels, the graft passer is removed and interference screws are inserted into the tibial tunnel through a first incision and through the thigh downwardly into the femoral tunnel. See, for example, U.S. Pat. No. Des. 309, 499.

Additional objects, features, and advantages of the invention will become apparent to those skilled in the art upon consideration of the following detailed descriptions of a preferred embodiment exemplifying the best mode of carrying out the invention as presently perceived.

BRIEF DESCRIPTION OF THE DRAWINGS

The detailed descriptions particularly refers to the accompanying figures in which.

DETAILED DESCRIPTION OF THE DRAWINGS

Endoscopic ACL reconstruction with bone-patellar tendon-bone graft replacement ligaments is a very beneficial but also a technically demanding procedure. Many issues create these technical challenges and these are listed as follows: 1) Divergence of the femoral interference screw in the femoral tunnel is common resulting in potential reduction in fixation; 2) Interference screw insertion into the femoral tunnel can also cause laceration of the patella tendon graft; and 3) Loss of fluid distention of the joint at critical times during the procedure is visually frustrating and may affect the outcome of the procedure. The graft passer apparatus and surgical method of the present invention uses a specially designed graft passer in the form of a protective tube or sheath which addresses these concerns. Through the utilization of an inexpensive, disposable graft passer component and the associated surgical technique, adequate distention of the joint is maintained particularly during femoral interference screw insertion, allowing excellent visualization throughout the procedure. The graft passer sheath allows insertion of a cannulated 7 mm femoral interference screw directly through the tibial tunnel without fear of damaging the tendinous portion of replacement ligament graft. Direct insertion of the femoral screw through the tibial tunnel also helps minimize tunnel/screw divergence. The graft passer of the present invention helps make endoscopic ACL reconstruction an easier, safer, and more reliable procedure.

Prior to the surgical procedure to replace the ACL, an uninflated Steri-Cuff™ disposable tourniquet cuff available from DePuy, Inc. in Warsaw, Ind. is applied to the patient's thigh. An arthroscopic leg holder is loosely applied and angled slightly cephalad to expose the anterior thigh maximally. This allows passage of the exiting guide pin later in the procedure. The foot of the operating table is flexed to allow 90–100 degrees of knee flexion. An arthroscopy pump may be used to facilitate the procedure and is recommended.

The tourniquet is generally inflated after the knee is prepped and draped. If an arthroscopy pump is used, tourniquet inflation can wait until the actual ACL reconstruction begins. Routine diagnostic arthroscopy is then performed to establish the extent of intra-articular damage. Meniscal pathology is identified and addressed with appropriate manual or power instrumentation. Meniscal repair sutures can be placed but are not tied until the ACL reconstruction is completed.

Figure 1:
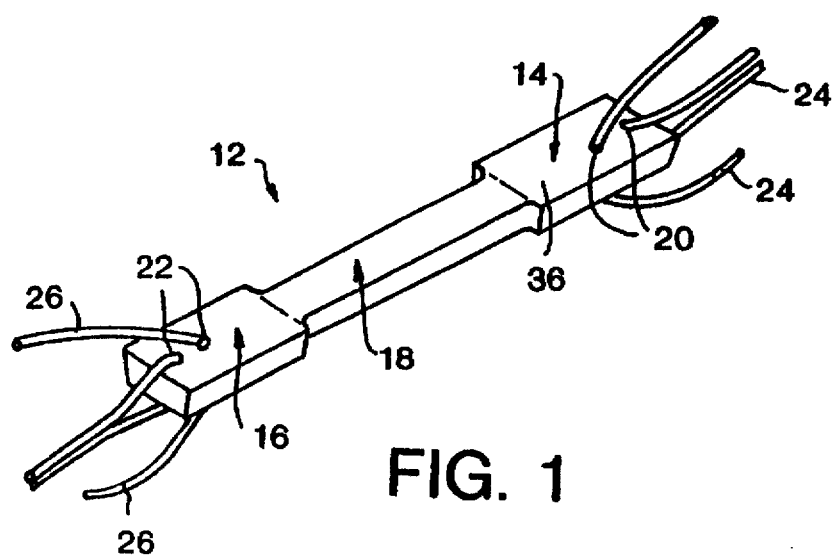
FIG. 1 is a perspective diagrammatical illustration of a bone-tendon-bone graft replacement ligament which has been harvested in a conventional manner.

A replacement ligament graft is typically harvested from the knee of the patient prior to replacement of the ACL. It is understood, however, that other types of replacement ligaments can be used in accordance with the present invention. The middle ⅓ of the patellar tendon is harvested through a midline incision utilizing an ACL Graft Knife available from DePuy to expedite the harvest and to provide consistently prepared grafts. The most common graft width is 10 mm with bone plugs from the patella and tibial tubercle. An illustrative bone-tendon-bone graft 12 is illustrated in FIG. 1. The replacement ligament graft 12 includes a femoral bone plug 14 and a tibial bone plug 16 connected by a tendon 18. Two oblique drill holes 20 and 22 are placed in bone plugs 14 and 16, respectively, prior to harvesting. A combination of osteotomes and an oscillating saw is used to harvest the bone plugs, 25 mm in length, while maintaining a trapezoidal shape. Two #1 size sutures 24 and 26 are placed through the holes 20 and 22, respectively, formed in each bone plug 14 and 16.

The bone plugs 14 and 16 are sized with a graft sizer such as a DePuy Graft Sizer to determine the necessary reamer size. The bone plugs 14 and 16 should comfortably slide through the sizing tubes of the graft sizer. If any resistance is felt, the next larger size is selected or the bone plugs can be trimmed if necessary. The graft sizer is translucent to allow visualization of area on the plugs 14 and 16 that require additional trimming. The appropriate tibial reamer or tunnel drill 48 has a diameter one millimeter larger than the largest bone plug. Ideally, both bone plugs will have the same diameter, but if not, the smaller diameter plug should be used for the femoral tunnel. Use of the double bladed ACL Graft Knife can ensure that both bone plugs have generally the same diameter. An appropriately sized graft passer sheath 10 is determined by the diameter of the bone plugs and the tibial tunnel. The diameter size of the graft passer sheath 10 is about 0.5 mm larger than the bone plugs 14 and 16 and about 0.5 mm smaller than the tunnel drill 28. For example, a 9.5 mm sheath is selected for a 9 mm tibial bone plug and a 10 mm tunnel drill 48 since the sheath is slightly undersized to facilitate passage through the tibial tunnel 50, yet large enough to accept the bone plugs 14 and 16.

Figure 2:
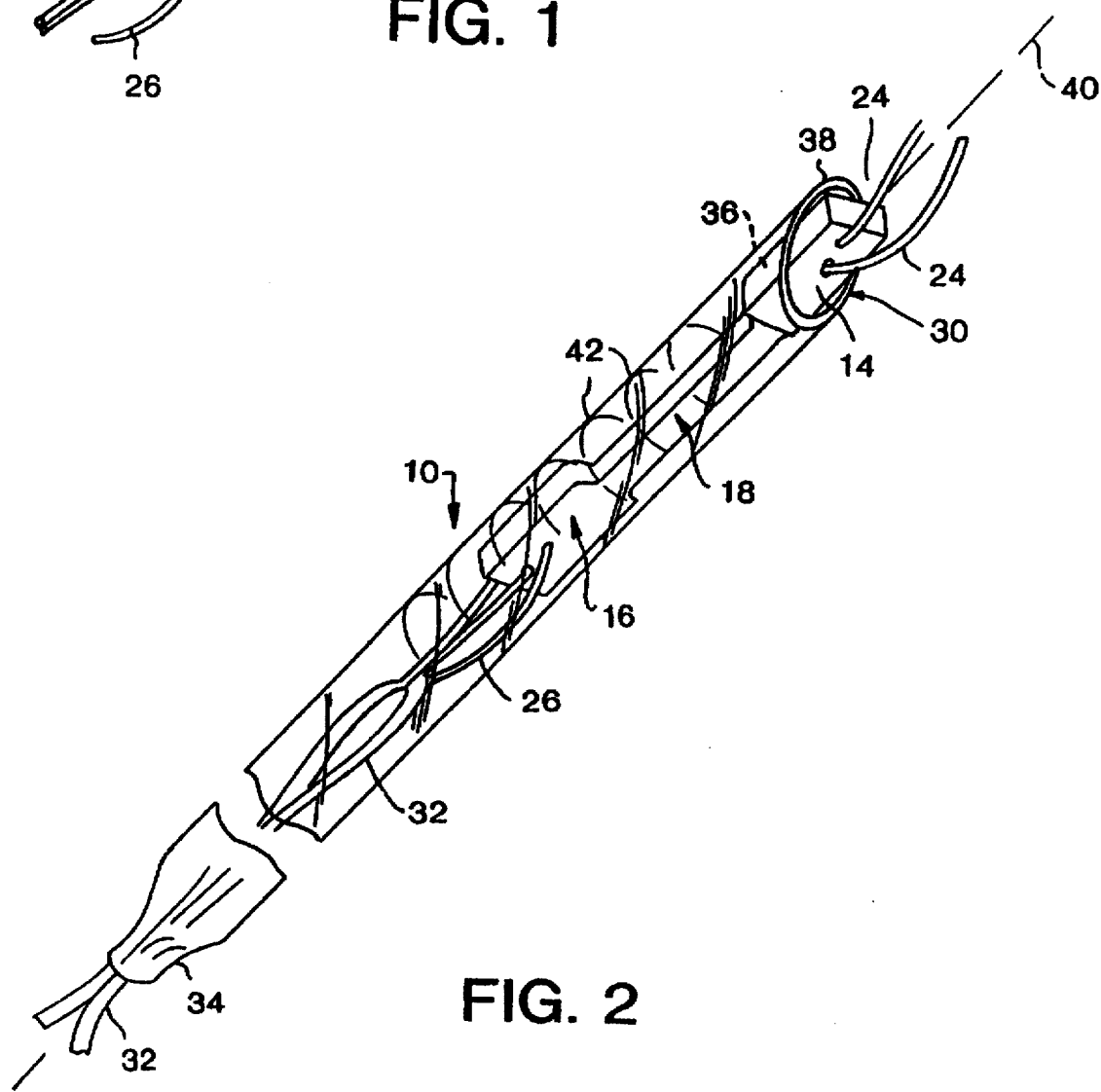
FIG. 2 is a perspective view of the replacement ligament graft passer apparatus of the present invention with the replacement ligament of FIG. 2 installed therein.

The intended tibial tunnel bone plug 16 may be inserted into an open end 30 of the sheath 10 as illustrated in FIG. 2 first by pulling the lead sutures 26 through the sheath 10 with a ribbon or tape 32 located inside sheath 10. Tape 32 is held within sheath 10 by a crimped end 34 located opposite from open end 30. The entire replacement ligament graft is then slid fully into the sheath 10. The cortical bone 36 of the femoral bone plug 14 is preferably situated under the pointed leading edge 38 of the sheath 10. Open end 30 of sheath 10 is cut at an angle relative to a longitudinal axis 40 of sheath 10 to provide the pointed leading edge 36. Preferably, sheath 10 is transparent and has a markings or a calibration scale 42 printed on a side wall of the sheath 10. The total length of the replacement ligament graft 12 as well as the length of the femoral bone plug 14 can be determined using the measurement lines 42 printed on the sheath 10. The prepared graft 12 enclosed in sheath 10 is then placed in saline to await placement within the tunnel.

The arthroscope is reinserted through the anterolateral portal and remnants of the original ACL are completely removed. A notchplasty must be performed in each case to avoid impingement and to improve visualization. The lateral femoral condyle is carefully tapered posteriorly with the use of hand instruments, motorized abraders, and shavers until the very posterior portion of the condyle is visualized. While fibrous tissue usually marks the posterior edge of the condyle. A probe or femoral offset aimer is also utilized to confirm this position. A small indentation in the lateral femoral condyle is made with an abrader or awl at the intended placement of the femoral guide pin. This is usually at the 11 o'clock position for a right knee, at the 1 o'clock position in the left knee, and about 5–6 mm anterior to the posterior edge of the femoral condyle.

Figure 3:
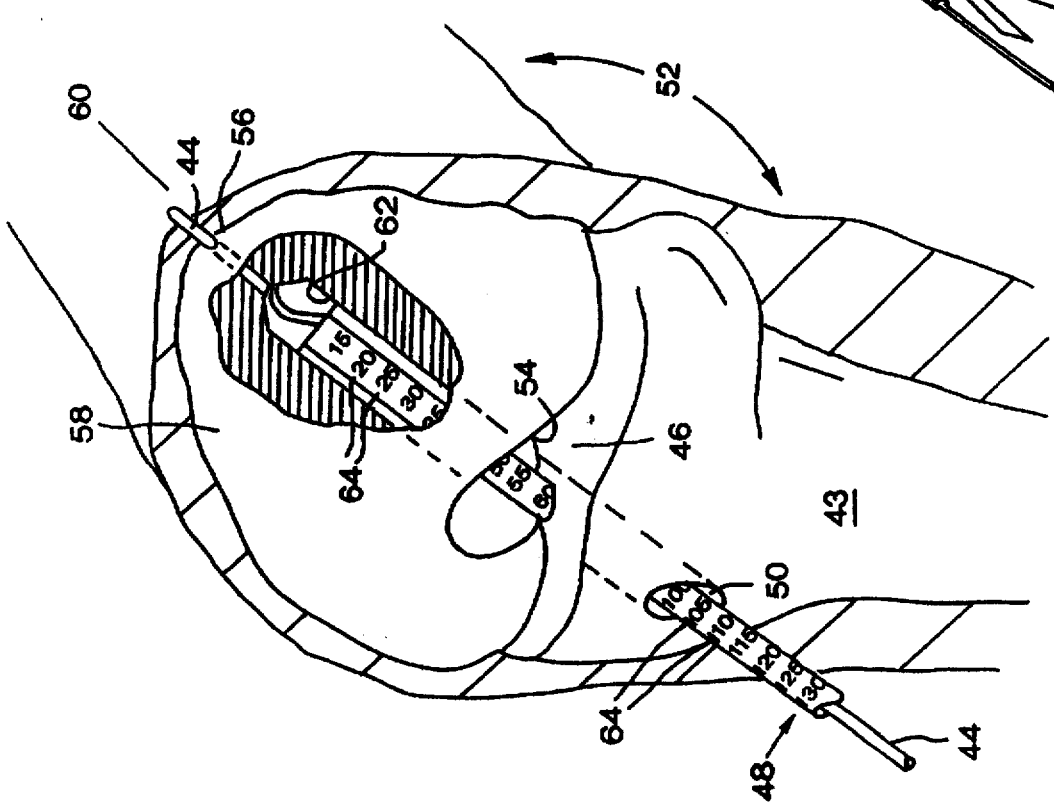
FIG. 3 is a diagrammatical illustration of a front view of a knee in which the anterior cruciate ligament is to be replaced illustrating a guide pin inserted through an anterior portion of the tibia, upwardly through the tibial plateau, and through a distal end of the femur to establish the position of a tunnel to be formed through the knee, and a tunnel drill inserted over the guide pin in the knee to form the tibial and femoral tunnels for receiving the replacement ligament.

The tip of the tibial drill guide (not shown) is inserted through the anteromedial portal. The tip of the guide is placed just anterior to the medial tibial spine. The angle of the guide is adjusted to allow for the variable placement of the medial portal and anatomic variations that may be present in the knee. The guide should start the tibial tunnel about 2–3 cm below the medial joint line. The flare of the anteromedial tibia is exposed subperiosteally and the guide is locked in position. A bayonet point pin 44 illustrated in FIG. 3 is then drilled into the tibia 43 while viewing the exit point on the tibial plateau 46 arthroscopically.

The position of pin 44 can be adjusted if necessary. A cannulated reamer 48 selected earlier is used to ream the tibial tunnel 50. The tunnel 50 is then plugged with an appropriately sized tunnel plug or universal cannula (not shown) to minimize fluid egress and maintain joint distention. Excess tissue and debris is removed from the joint side of the tunnel 50, and the edges of the tunnel 50 are smoothed.

Bayonet point pin 44 is then placed through the universal cannula and into the joint by hand. With the knee flexed at least 70 degrees illustrated by angle 52, the pin 44 is placed by hand into the preselected position on the lateral femoral condyle 54 and lightly tapped into position with a mallet. A drill is then placed on the pin 44 and the pin 44 is drilled through the anterolateral cortex 56 of the femur 58 and exits the thigh 60. The universal cannula is then removed from the tibial tunnel 50 exit, and the femoral tunnel 62 is now ready for reaming. The diameter of the femoral reamer 48 is determined by the size of the femoral bone plug 14. The femoral tunnel 62 can be the same size or smaller than the tibial tunnel 50 diameter, but not larger. The length of the femoral tunnel 62 determines the position of the tibial bone plug 16 in relation to the tibial tunnel 50. The following technique is used to ensure that the tibial bone plug 16 is fully enclosed in the tibial tunnel 50 to accept interference screw fixation. The total length of the entire bone-patellar tendon-bone graft 12 is read from the measurement lines 42 on sheath 10. The femoral tunnel 52 is then reamed to a depth 5 mm longer than the length of the femoral bone plug 14. The depth of the femoral tunnel can be seen arthroscopically utilizing measurement lines 64 on the reamer 48. The total depth of the reamer 48 within the knee can now be read from the measurement lines 64 marked on the reamer 48 external to the tibial tunnel 50. Further reaming of the femoral tunnel 62 may be necessary until the depth of reamer 48 is at least equal to the total length of the graft 12. If counter-sinking the femoral tunnel 62 more than 5 mm is necessary, then the femoral tunnel diameter must be the same as the tibial tunnel 50 to allow the sheath 10 to fit inside the femoral tunnel 62. Bone debris is removed from the joint and tunnels.

Figure 4:
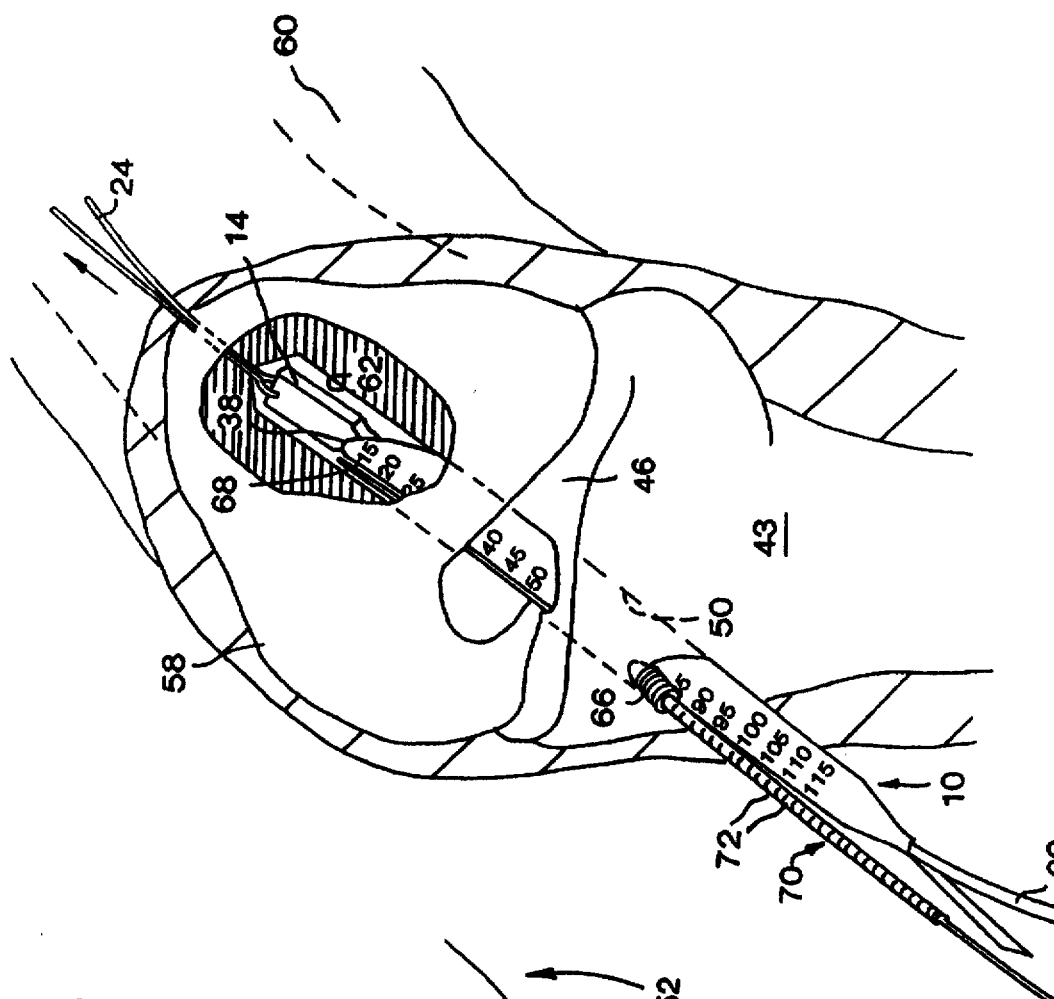
FIG. 4 is a diagrammatical illustration of the knee of FIG. 3 in which the graft passer and replacement ligament have been inserted upwardly into the tunnel, the femoral bone plug has been advanced past an open end of the graft passer sheath into the femoral tunnel, and wherein a guide pin has been inserted through the tunnel outside the graft passer sheath for guiding placement of a first interference screw through the tibial tunnel and into the femoral tunnel to secure the femoral bone plug within the femoral tunnel.

The lead sutures 24 of the graft 12 are placed through an eyelet (not shown) of the bayonet point pin 44 which has remained in place. The bayonet pin 44 is then manually pulled out of the thigh 60 bringing the lead sutures 24 into position. The sheath 10, with the fully enclosed graft 12 is then placed into the tibial tunnel 50 as a unit. Loss of fluid from the tibial tunnel is immediately reduced when the graft passer sheath 10 is within the tibial tunnel and fluid distension of the joint reoccurs. A synchronized combination of pushing the sheath 10 and gently pulling the lead sutures 24 brings the graft 12 and sheath 10 into the joint as illustrated in FIG. 4. The low friction properties of the wet sheath 10 allows for easy and quick placement. The longer leading edge 38 of the sheath 10, with the measurement lines 42, is then brought up to the femoral tunnel 62. Typically, sheath 10 is not inserted into femoral tunnel 62 unless required based on the length of graft 12. The sheath 10 and graft 12 can be rotated to adjust the position of the graft 12 before the femoral bone plug 14 enters the femoral tunnel 62. The lead sutures 24 are then pulled to move femoral bone plug 14 past open end 30 of sheath 10 to seat the femoral bone plug 14 fully into the femoral tunnel 62 as illustrated in FIG. 4. The graft 12 is now ready for fixation with interference fixation screws. Illustratively, Advantage Kurosaka™ screws available from DePuy, Inc. are used. The sheath 10 remains in position as the femoral interference screw 66 is placed.

Figure 5:
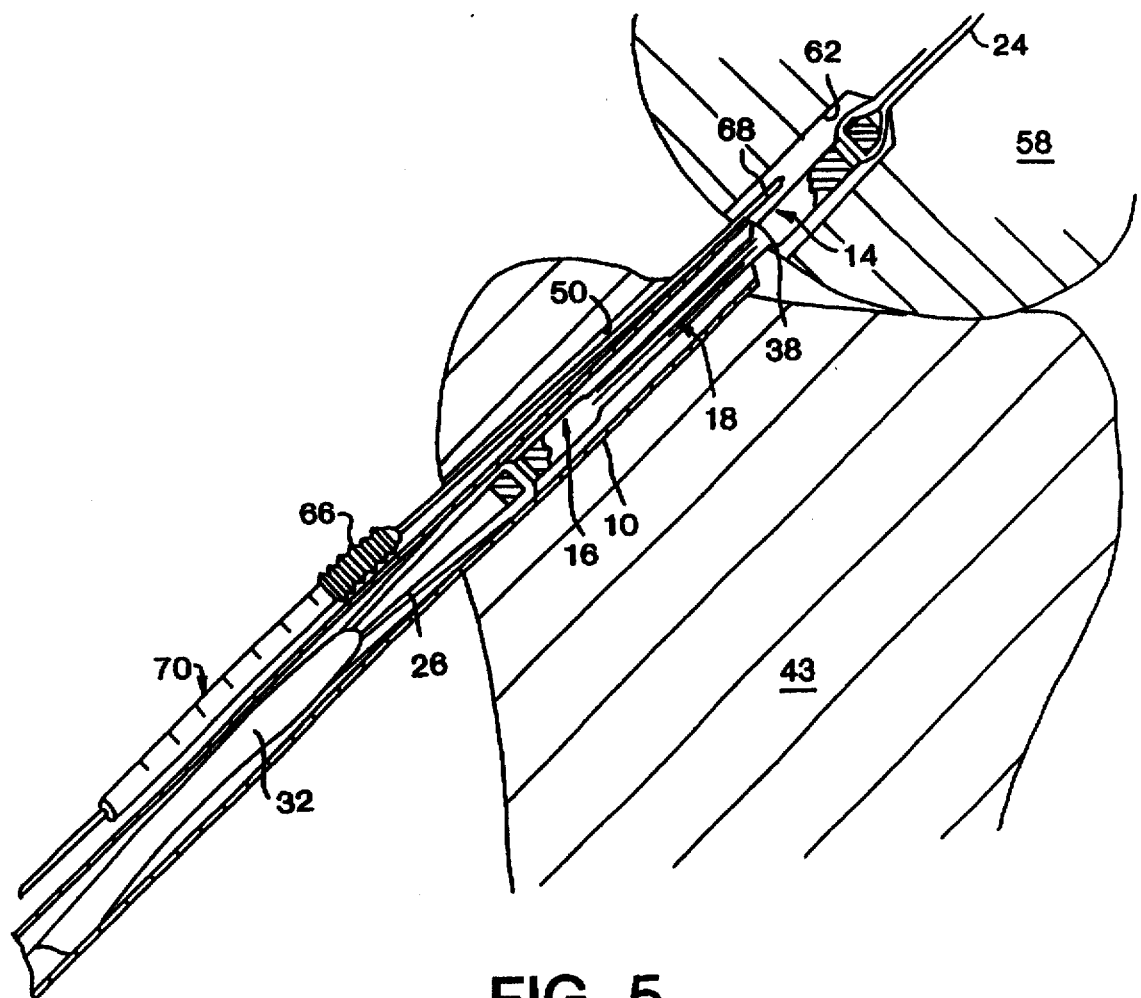
FIG. 5 is a sectional view taken through the knee of FIG. 4.

The longer edge 38 of the sheath 10 is positioned in the femoral tunnel 62 at the same depth as the femoral tunnel 62 was countersunk to protect the tendinous portion 18 of the graft 12. An appropriate guide pin 68 is placed through the tibial tunnel 50 outside of the sheath 10 and fed completely into the femoral tunnel 62. Illustratively, pin 68 illustrated in FIGS. 4 and 5 is a Model No. 2952-63 pin having a 0.062 inch diameter with rounded ends available from DePuy. The knee should be flexed at 70–90 degrees. A 7 mm diameter cannulated interference screw 66 (allows use of 0.062" guidewire) is utilized if direct placement of the screw 66 through the tibial tunnel 50 is performed. A 20–25 mm screw length is utilized given a 25 mm bone plug. A cannulated screw driver 70 is then used to insert the 7 mm screw 66 over the guidewire 68 at the tibial tunnel 50. It should be noted that the shaft diameter of the screwdriver 70 may be preferably be the same size or smaller than the root diameter of the screw 66. This parameter may be designed into the system of the present invention. Screwdriver 70 includes measurement lines 72 printed on an outer surface along its axis. The sheath 10 protects the tendinous portion 18 of the graft 12 even in the tibial tunnel 50 during insertion of screw 66. Compression of the tibial bone plug 16 from the passing 7 mm femoral screw 66 is irrelevant due to the fact that a 9 mm interference screw 74 is used to affix the tibial bone plug 16 in tibial tunnel 50.

Figure 6:
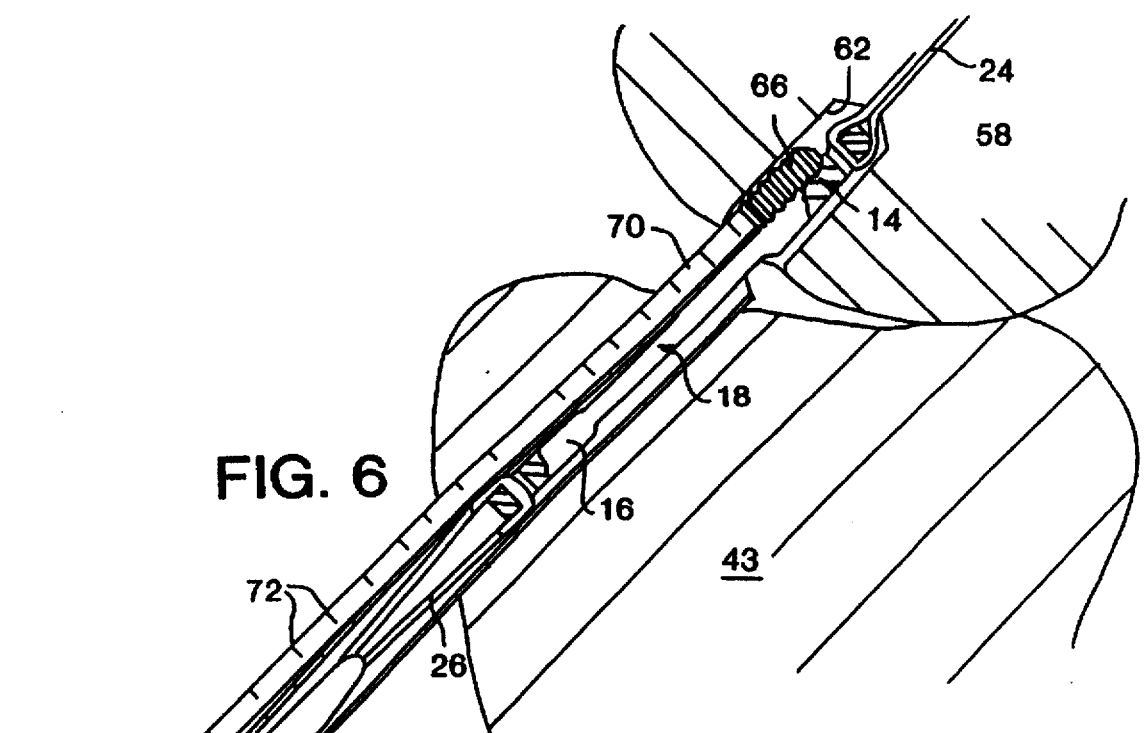
FIG. 6 is a sectional view similar to FIG. 5 illustrating the first interference screw installed within the femoral tunnel using an appropriate driver passing over the guide pin.
Figure 7:
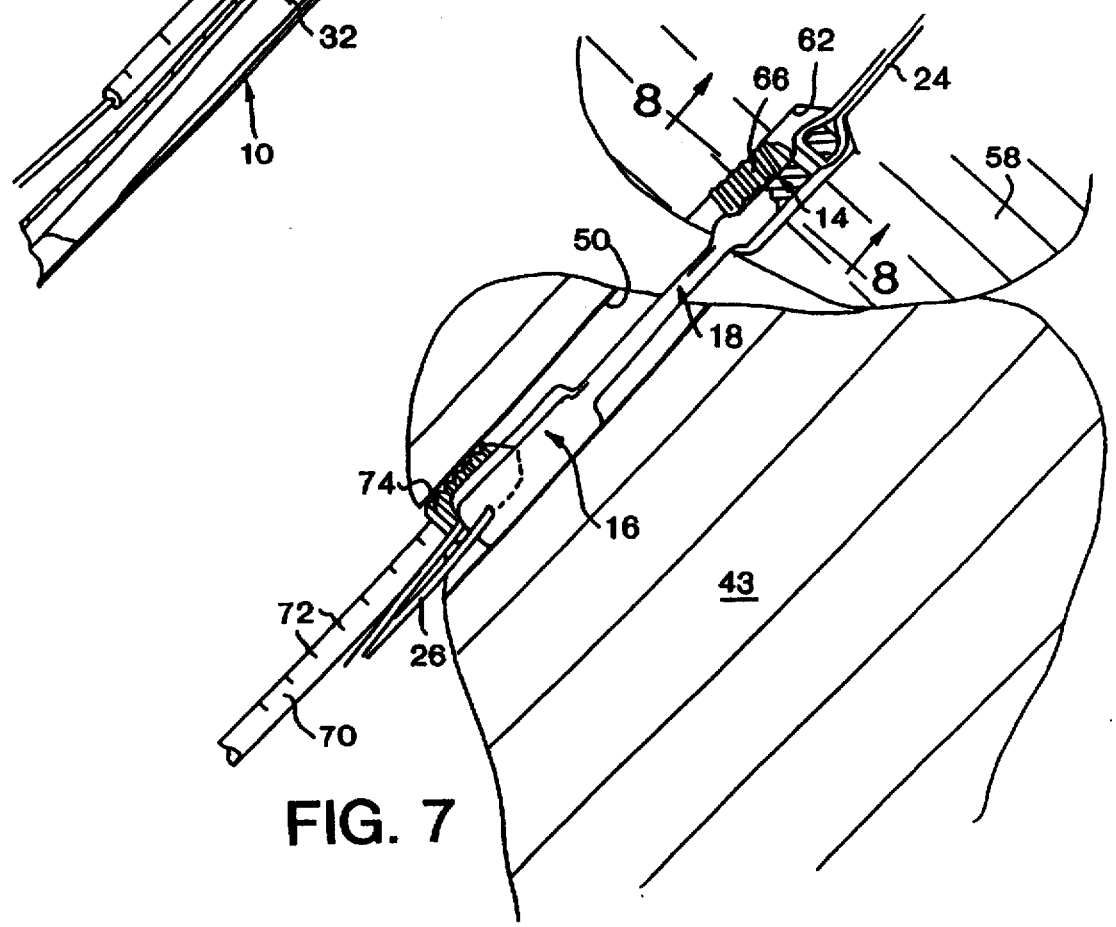
FIG. 7 is a diagrammatical illustration similar to FIGS. 5 and 6 illustrating insertion of a second interference screw into the tibial tunnel to secure the tibial bone plug within the tibial tunnel.
Figure 8:
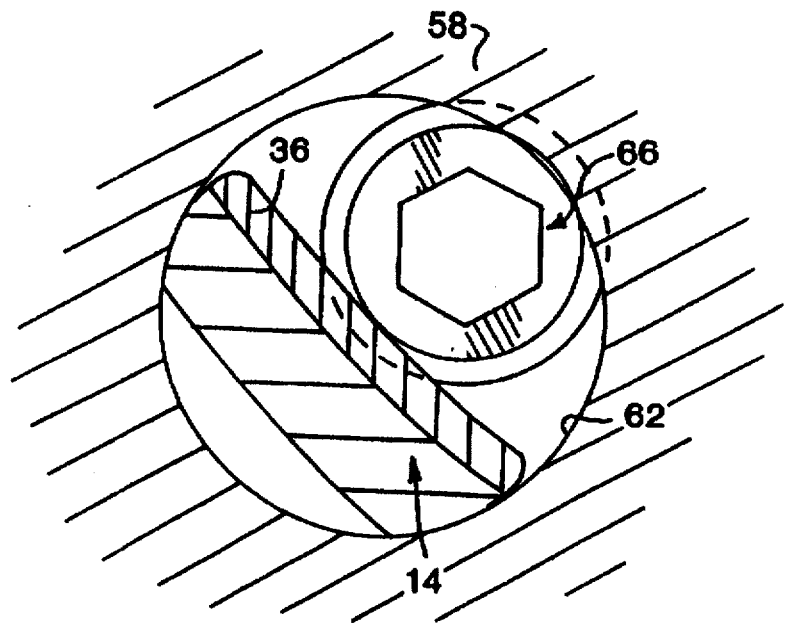
FIG. 8 is a transverse sectional view taken along lines 8—8 of FIG. 7 diagrammatically illustrating the interference screw engaging cortical bone of the bone plug to force the bone plug against the side wall of the tunnel to promote healing of the bone plug inside the femoral tunnel.

Once the screw 66 is completely in the knee joint, the tapered tip of the interference screw 66 continues into the femoral tunnel 62. Screw 66 is advanced and buried to a depth within femoral tunnel 62 that avoids impingement on the tendinous portion 18 of the graft 12 as illustrated in FIG. 6. This can be checked arthroscopically with the measurement lines 72 on the screwdriver 70. The sheath 10 allows placement of the interference screw 66 on the cortical side 36 of the bone plug 14 allowing cancellous to cancellous bone fixation. This is best illustrated in FIG. 8.

Figure 9:
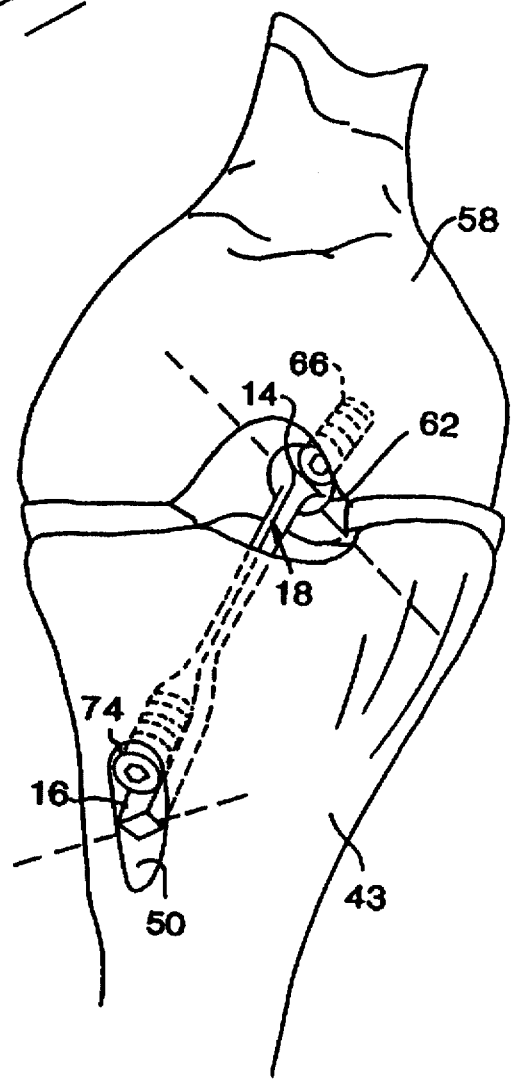
FIG. 9 is a diagrammatical illustration of a front view illustrating the position of the first interference screw inside the femoral tunnel and the second interference screw inside the tibial tunnel.

The knee is placed through a range of motion with the sheath 10 in position and tension on the distal sutures 26 to check for graft impingement. If indicated, further notchplasty can now be done with the protective sheath 10 still in position. The sheath will also serve to protect the graft 12 from the instruments used during additional notchplasty. The sheath 10 is then removed completely by simply pulling it distally out of the tibial tunnel. A 9 mm diameter×20–25 mm cannulated interference screw 74 is inserted into the tibial tunnel 50 while maintaining proper tension on the graft 12 with the knee flexed at 15 degrees. The position of screws 66 and 74 is illustrated in FIG. 9. The tendon portion 18 of replacement ligament 12 is twisted slightly within the knee. Stability and range of motion of the knee are again checked. The knee is usually drained postoperatively and compression ice wraps are then applied to reduce swelling. Postoperative care is then up to the individual surgeons preference.

The use of the ligament sheath 10 has several distinct and unique advantages that provide substantial benefits in endoscopic ACL reconstructions. The graft 12 is fully protected throughout the procedure and especially during the critical femoral interference screw 66 insertion. Direct insertion of the femoral interference screw 66 through the tibial tunnel 50 is possible with less chance for screw/tunnel divergence in the femur 58. Further notchplasty can also be accomplished once the graft is in position without fear of harming the graft. Fluid distention of the joint is maintained with the sheath in position, improving visibility and safety during critical portions of the procedure. Handling the graft 12 is easy once placed within the sheath 10 and it also reduces risk of contamination during surgery. Calibrated markings 64 and 42 on the reamer 48 and sheath 10, respectively, provide easy determination of required femoral tunnel depth. Use of the disposable graft passer 10 of the present invention reduces operating time, provided subsequent cost savings, and provides consistent results.

Although the invention has been described in detail with reference to a certain preferred embodiment, variations and modifications exist within the scope and spirit of the present invention as described and defined in the following claims.

What is claimed is:

1. A method for installing a bone-tendon-bone graft in substantially coaxial tibial and femoral tunnels formed in a knee joint by drilling and reaming upwardly from the anterior surface of the tibia below its plateau, through the plateau, and into the distal end of the femur, the bone-tendon-bone graft including a tibial bone plug, a femoral bone plug, and a tendon portion extending therebetween, the method comprising the steps of:

providing an elongated sheath having a leading open end, and an opposite end, the sheath having an outer diameter smaller than an internal diameter of the tibial and femoral tunnels and an inner diameter larger than a maximum thickness of the graft;

loading the graft into the leading open end of the sheath to place the entire graft fully into the sheath with the femoral bone plug of the graft located generally adjacent the leading open end of the sheath;

inserting the sheath with the graft therein upwardly through the tibial tunnel to position the leading edge of the sheath and the femoral bone plug generally adjacent a mouth of the femoral tunnel;

moving the graft partially out of the sheath so that femoral bone plug moves upwardly into the femoral tunnel;

installing an elongated guide pin upwardly through the tibial and femoral tunnels outside the sheath;

installing a first cannulated interference screw into the femoral tunnel by inserting the first interference screw over the guide pin, threading the first interference screw upwardly through the tibial tunnel, and threading the first interference screw into the femoral tunnel so that a longitudinal axis of the first interference screw is substantially parallel to and spaced apart from a longitudinal axis of the femoral tunnel, the first interference screw engaging the femoral bone plug to force it against a wall of the femoral tunnel for bone fixation;

removing the sheath axially out of the tibial tunnel leaving the tibial bone plug in the tibial tunnel; and inserting a second interference screw into the tibial tunnel to force the tibial bone plug against a wall of the tibial tunnel for bone fixation.

2. The method of claim 1, wherein the leading open end of the sheath is formed in a plane at an acute angle relative to a longitudinal axis of the sheath to provide a generally pointed leading edge.

3. The method of claim 1, wherein the sheath has a calibrated scale printed thereon starting at the leading open end.

4. The method of claim 1, further comprising the step of performing notchplasty on a femoral notch with the sheath still in place after the step of inserting the first interference screw to protect the tendon portion of the graft during the notchplasty.

5. The method of claim 1, further comprising the step of moving the knee joint through a range of motion with the sheath still in place after the step of inserting the first interference screw to protect the tendon portion while checking for impingement of the first interference screw on the tendon portion of the graft.

6. The method of claim 1, wherein the step of installing the first interference screw includes the step of providing a screwdriver having a shaft for driving the first interference screw, the shaft having a diameter smaller than a minimum diameter of threads on the first interference screw, the shaft being cannulated to slide over the guide pin.

7. The method of claim 6, wherein the shaft of the screwdriver includes a calibrated scale printed thereon.

8. The method of claim 1, wherein the first interference screw has a diameter smaller than a diameter of the second interference screw.

9. The method of claim 8, wherein the diameter of the first interference screw is about 7 mm and the diameter of the second interference screw is about 9 mm.

10. An apparatus for use in installing a replacement ligament in substantially coaxial tibial and femoral tunnels formed in a knee joint by drilling upwardly from the anterior surface of the tibia below its plateau, through the plateau, and into the distal end of the femur, said replacement ligament having a leading end portion receivable in the femoral tunnel and a trailing end portion receivable in the tibial tunnel, said apparatus comprising a sheath having a leading open end and an opposite end, the sheath having a calibrated scale printed thereon starting at the leading open end, the calibrated scale providing a visual indication of a distance from the leading open end of the sheath, said sheath being configured to receive the replacement ligament therein while the sheath is outside a patient's body with the leading end portion of the replacement ligament adjacent said open end and with the trailing end portion of the replacement ligament disposed toward said opposite end of the sheath, the sheath being sized for insertion into the tibial tunnel to position the replacement ligament within the knee joint.

11. The apparatus of claim 10, wherein the sheath is transparent to permit visual inspection of the replacement ligament within the sheath.

12. An apparatus for use in installing a replacement ligament in substantially coaxial tibial and femoral tunnels formed in a knee joint by drilling upwardly from the anterior surface of the tibia below its plateau, through the plateau, and into the distal end of the femur, said replacement ligament having a leading end portion receivable in the femoral tunnel and a trailing end portion receivable in the tibial tunnel, said apparatus comprising a sheath having a leading open end and an opposite end, the leading open end of the sheath being formed in a plane aligned at an acute angle relative to a longitudinal axis of the sheath to provide a generally pointed leading edge, said sheath being configured to receive the replacement ligament therein while the sheath is outside a patient's body with the leading end portion of the replacement ligament adjacent said open end and with the trailing end portion of the replacement ligament disposed toward said opposite end of the sheath, the sheath being sized for insertion into the tibial tunnel to position the replacement ligament within the knee joint.

13. The apparatus of claim 12, wherein the sheath has a calibrated scale printed thereon starting at the generally pointed leading open edge, the calibrated scale providing a visual indication of a distance from the leading open end of the sheath.

14. The apparatus of claim 13, wherein the sheath is transparent to permit visual inspection of the replacement ligament graft within the sheath and to permit a determination of the length of the replacement ligament using the calibrated scale printed on the sheath.

15. An apparatus for use in installing a replacement ligament in substantially coaxial tibial and femoral tunnels formed in a knee joint by drilling upwardly from the anterior surface of the tibia below its plateau, through the plateau, and into the distal end of the femur, said replacement ligament having a leading end portion receivable in the femoral tunnel and a trailing end portion receivable in the tibial tunnel, said apparatus comprising a sheath having a leading open end and an opposite end, said sheath being configured to receive the replacement ligament therein while the sheath is outside a patient's body with the leading end portion of the replacement ligament adjacent said open end and with the trailing end portion of the replacement ligament disposed toward said opposite end of the sheath, the sheath being sized for insertion into the tibial tunnel to position the replacement ligament within the knee joint, and a ribbon located within the sheath to facilitate insertion of the replacement ligament into the sheath, the opposite end of the sheath being crimped to retain the ribbon within the sheath.

16. A method for installing a replacement ligament in a knee joint including a tibia and femur, the method comprising the steps of:

providing an elongated sheath having a leading end and an opposite end;

loading the replacement ligament in the sheath;

drilling upwardly from an anterior surface of the tibia, through the tibial plateau, and into the distal end of the femur to form a tibial tunnel and a femoral tunnel substantially aligned on a single tunnel axis;

inserting the sheath with the replacement ligament therein upwardly through the tibial tunnel to position the leading end of the sheath adjacent a mouth of the femoral tunnel;

moving the replacement ligament partially out of the sheath so that a portion of the replacement ligament moves upwardly into the femoral tunnel;

inserting a first interference screw through the tibial tunnel outside the sheath and threading the first interference screw into the femoral tunnel so that a longitudinal axis of the first interference screw is aligned substantially parallel to and spaced apart from the tunnel axis to secure the replacement ligament within the femoral tunnel;

removing the sheath from the tibial tunnel; and inserting a second interference screw into the tibial tunnel to secure a portion of the replacement ligament within the tibial tunnel.

17. The method of claim 16, wherein the first interference screw has a diameter smaller than a diameter of the second interference screw.

18. The method of claim 17, wherein the diameter of the first interference screw is about 7 mm and the diameter of the second interference screw is about 9 mm.

19. The method of claim 16, wherein the leading end of the sheath is formed as an open end in a plane at an acute angle relative to a longitudinal axis of the sheath to provide a generally pointed leading edge.

20. The method of claim 16, wherein the sheath has a calibrated scale printed thereon starting at the leading open end thereof, the calibrated scale providing a visual indication of a distance from the leading open end of the sheath.

21. The method of claim 16, further comprising the step of performing notchplasty on a femoral notch with the sheath still in place after the step of inserting the first interference screw to protect the tendon portion of the graft during the notchplasty.

22. The method of claim 16, further comprising the step of moving the knee joint through a range of motion with the sheath still in place after the step of inserting the first interference screw to protect the tendon portion with checking for impingement of the first interference screw on the tendon portion of the graft.

23. The method of claim 16, further comprising the step of installing an elongated guide pin upwardly through the tibial and femoral tunnels outside the sheath before the step of inserting the first interference screw, the first interference screw being cannulated to move over the elongated guide pin.

* * * * *